United States Patent [19]

Vesterager et al.

[11] 4,274,418
[45] Jun. 23, 1981

[54] ELECTROCHEMICAL MEASURING DEVICE

[75] Inventors: Peter K. R. Vesterager, Maaløv; Børge Jeppesen, Glostrup, both of Denmark

[73] Assignee: Radiometer A/S, Copenhagen, Denmark

[21] Appl. No.: 45,689

[22] Filed: Jun. 5, 1979

Related U.S. Application Data

[63] Continuation of Ser. No. 802,113, May 31, 1977, abandoned.

[30] Foreign Application Priority Data

Jun. 1, 1976 [DK] Denmark ............................ 2398/76

[51] Int. Cl.³ ................................................ A61B 5/00
[52] U.S. Cl. ................................ 128/635; 204/195 B; 204/195 P
[58] Field of Search .................. 128/635, 632, 640; 204/195 P, 195 B

[56] References Cited

U.S. PATENT DOCUMENTS

| | | | |
|---|---|---|---|
| 3,187,745 | 6/1965 | Baum et al. | 128/640 |
| 3,580,239 | 5/1971 | Watanebe et al. | 128/635 |
| 3,659,586 | 5/1972 | Johns et al. | 128/635 |
| 3,795,239 | 3/1974 | Eberhard et al. | 128/635 |
| 3,875,037 | 4/1975 | Krull | 204/195 P |
| 3,918,434 | 11/1975 | Lubbers | 128/635 X |
| 3,998,212 | 12/1976 | Reichenberger | 128/635 |
| 4,005,700 | 2/1977 | Parker | 128/632 |

OTHER PUBLICATIONS

Vesterager, "Continuous Trans. Measurement ... Po₂", *Measurement of Oxygen*, 1976.
Huch et al., "Transcutaneous Measurement of Blood Po₂", J. Pernat. Med., 1 (1973), 183.
Johns et al., "A System ... Ventilation", Bio-Med. Sciences Inst., Sixth Net. Symp., May 1968, pp. 119-121.
Eberhard et al., "Continuous Po₂ ... Electrodes", Med. & Bio. Eng., vol. 13, pp. 436-442, May 1975.

*Primary Examiner*—Lee S. Cohen
*Attorney, Agent, or Firm*—Robert E. Burns; Emmanuel J. Lobato; Bruce L. Adams

[57] ABSTRACT

The invention relates to an electrochemical measuring device for transcutaneous measurement of arterial partial gas pressure, especially partial pressure of oxygen or carbon dioxide. The measuring device comprises an annular mounting member having a skin contacting surface adapted to be fastened to the skin surface of a patient, and a sensor of the type having a semi-permeable membrane adapted to be releasably connected to the mounting member. In the connected position of the sensor, the membrane is axially spaced from the skin contacting surface of the mounting member so that the membrane, the inner wall of the annular mounting member, and the skin surface define a measuring chamber which may be filled with a gel or another medium, if desired.

8 Claims, 10 Drawing Figures

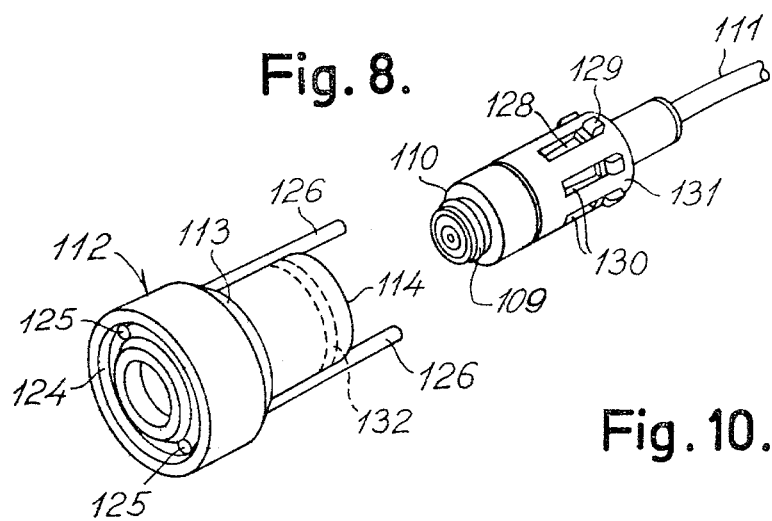
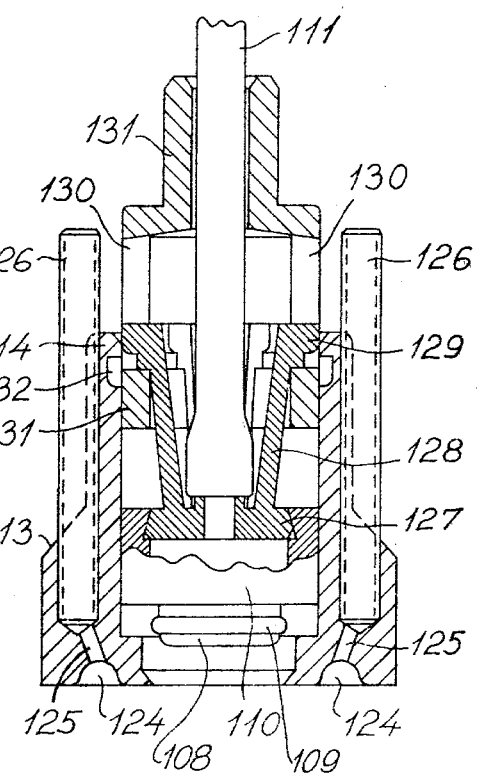
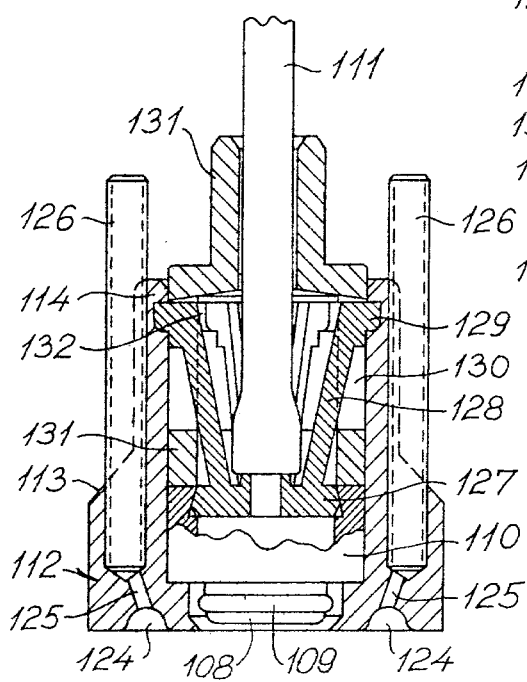

ELECTROCHEMICAL MEASURING DEVICE

This is a continuation of application Ser. No. 802,113, filed May 31, 1977, and now abandoned.

BACKGROUND OF THE INVENTION

1. Field of the Invention

Electrochemical measuring devices for transcutaneous measurement of gas, especially oxygen and carbon dioxide, diffusing from the blood vessels and through skin tissue, are known. On the basis of such a transcutaneous measurement of for example oxygen it is possible to estimate the arterial partial pressure of oxygen which may be of vital importance, for example in surveying the condition of new-borns and of patients under anaesthesia.

2. Description of the Prior Art

The measuring device according to the invention is of the type comprising a sensor having a semi-permeable membrane, and an annular skin contacting surface encircling at least part of said membrane and adapted to be fastened to the skin of a patient with a membrane positioned adjacent to the skin. When such measuring device is to be used it is common practice to apply a drop of contact gel to the center of the membrane and to fasten the annular skin contacting surface to the skin of the patient by means of a double sided adhesive ring.

From time to time it is necessary to remove the measuring device from the skin of the patient in order to calibrate the sensor and/or to replace the semi-permeable membrane by a new one. By such removal of the measuring device the adhesive connection between the skin and the skin contacting surface must be broken by tearing the measuring device from the skin. Such tearing off of the measuring device is, of course, rather unpleasant for the patient. Furthermore, after tearing off of the measuring device it is necessary to clean the skin contacting surface of the measuring device and the skin for adhesive residues before the measuring device may again be mounted on the skin of the patient after calibration of the sensor and/or replacement of the membrane and by means of a further double sided adhesive ring.

SUMMARY OF THE INVENTION

The present invention provides an electrochemical measuring device for transcutaneous measurement and comprises a sensor of the type having a part provided with a semi-permeable membrane, an annular mounting member having an annular skin contacting surface at one end adapted to be fastened to the skin of a patient, and connecting means for releasably connecting said sensor to the other end of said mounting member in a relative position in which said sensor part extends into the annular mounting member so that said membrane is axially spaced from said skin contacting surface. When the measuring device according to the invention is to be used, the skin contacting surface of the annular mounting member is fastened to the skin of the patient, for example by means of an adhesive ring. The sensor of the measuring device may now be releasably connected to the opposite end of the mounting member, whereby the semi-permeable membrane, the annular mounting member, and the skin area surrounded thereby define a closed measuring chamber. This measuring chamber is preferably, but not necessarily, filled with a liquid, such as a gel, or another suitable medium. Gases, such as oxygen and/or carbon dioxide, diffuse through the skin area defining said measuring chamber, and after a certain period of time the partial pressures of these gases in the measuring chamber become representative of the arterial partial gas pressures. The gas to be measured diffuses through the semi-permeable membrane into the sensor in which the partial pressure of the gas is measured in a known manner. The spacing between the membrane and the opposite skin area reduces or eliminates the risk that the membrane is exposed to detrimental local pressure due to direct skin contact and skin movements. The releasable connection between the mounting member and the sensor allows an easy removal of the sensor for calibration and/or membrane replacement or for other purposes. The sensor may later be remounted at exactly the same location at the patient's skin because the mounting member has not been removed therefrom. The medium used in the measuring chamber defined in the measuring device according to the invention may advantageously be of the same or a similar type as that in which the sensor is calibrated in vitro, whereby errors of measurement may be reduced.

In connection with electrodes for measuring electrical potentials it is known to use an annular mounting member of the type described above and defining a chamber which is filled with contact gel, vide for example U.S. Pat. No. 3,187,745. However, in this known electrode device the contact gel merely serves as an electrical conductor, and it was not obvious that a similar structure could advantageously be used in connection with an electrochemical measuring device of the type described above for transcutaneous measurement of partial gas pressures.

When the measuring device according to the invention is used at locations where a vacuum source is available the use of adhesive rings may be avoided and the mounting member may be adhered to the skin of the patient by vacuum. For that purpose one or more depressions or recesses may be formed in the skin contacting surface of the mounting member and adapted to be connected to a vacuum source. The connection between the depressions and the recesses and the vacuum source may be maintained as long as the mounting member should be fastened to the skin, or a non-return valve may be provided so that the connection to the vacuum source may be disconnected when a sufficient vacuum has been established in said recesses or depressions.

The sensor may be releasably connected to the mounting member in any suitable manner allowing a relatively easy and quick mounting and demounting and simultaneously securing a sufficiently reliable connection. As an example, the sensor may be removably connected to the mounting member by thread means formed on interengaging parts of the sensor and the mounting member, respectively. In order to facilitate mounting and demounting of the sensor the thread preferably extends over only a fraction of a complete turn. Alternatively, the sensor may be removably connectable to the mounting member by snap fastening means formed on interengaging parts of the sensor and mounting member, respectively. In the latter case it should be made sure that the force necessary for releasing the snap fastening connection is smaller than necessary for breaking the adhesive connection between the mounting member and the skin surface. This condition is fulfilled by snap fastening means comprising resilient detent means arranged on the sensor and engageable with an inner recess formed in the mounting member, a releasing member mounted on the sensor being displaceable in relation thereto between an engaging position in which the detent means are free to engage with the recess, and a releasing position in which the releasing member retains the detent means in a retracted, non-engaging position.

In order to relatively quickly obtain an equilibrium condition within the measuring chamber defined between the semi-permeable membrane and the skin surface of the patient this measuring chamber should be relatively small. Therefore, according to the invention the semi-permeable membrane is axially spaced 0.05–0.5 mm and preferably 0.1–0.5 mm from the skin contacting surface of the mounting member when the sensor is in its mounted position. The spacing may, for example, be chosen in dependence of thickness of the adhesive ring intended for use in fastening the mounting member to the skin surface.

BRIEF DESCRIPTION OF THE DRAWING

The invention will now be further described with reference to the drawing illustrating various embodiments of the measuring device according to the invention, and wherein FIG. 8 is a perspective view of another embodiment of the measuring device according to the invention, the sensor being separated from the mounting member, FIG. 9 is a sectional view of the embodiment shown in FIG. 8 in an enlarged scale and with the sensor connected to the mounting member, and FIG. 10 is the same as FIG. 9, but after release of the locking connection between the sensor and the mounting member.

DESCRIPTION OF THE PREFERRED EMBODIMENTS

Figure 1:
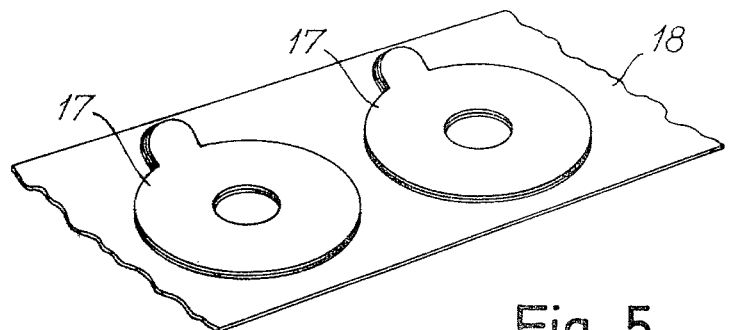
FIG. 1 is a sheet or foil on which double sided adhesive rings are arranged.
Figure 2:
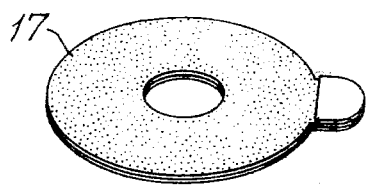
FIG. 2 is such an adhesive ring having the adhesive exposed on one side thereof.

The embodiments of the mounting device according to the invention shown in FIGS. 1-7 of the drawings comprise an electrode sensor or sensor unit 10 which by means of a cable 11 may be electrically connected to a suitable conventional measuring and registering equipment (not shown). The measuring device also comprises a mounting member or mounting ring 12 having a substantially radially extending flange 13 forming a skin abutment surface, and a substantially axially extending collar or neck 14 with an internal thread 15 adapted to cooperate with a thread 16 formed on the sensor 10 for releasably connecting the sensor to the mounting member 12.

Figure 3:
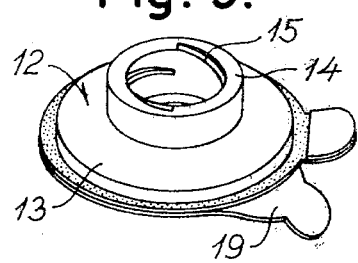
FIG. 3 is a mounting member forming part of one embodiment of the measuring device according to the invention and having an adhesive ring as that shown in FIG. 2 arranged on its skin contacting surface.
Figure 4:
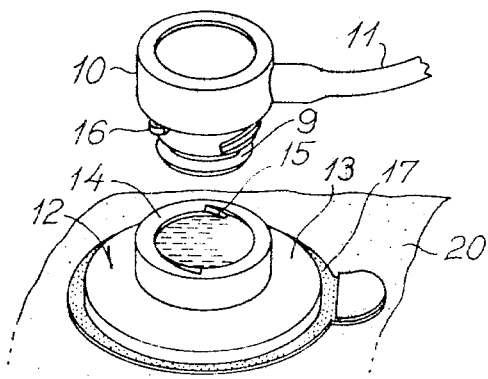
FIG. 4 is an electrode sensor which is about to be mounted on the mounting member as that shown in FIG. 3 and arranged on the skin surface.
Figure 5:
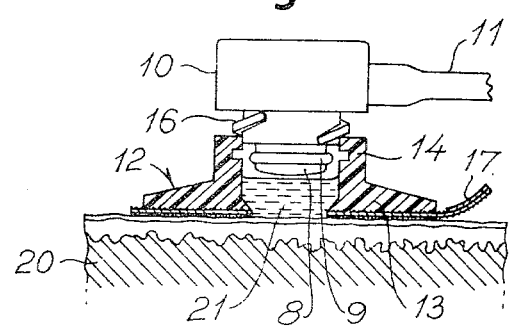
FIG. 5 is a side view and partial sectional view of the measuring device shown in FIG. 4, the electrode sensor having been brought in engagement with, but not completely connected to the mounting member.

The measuring device according to the invention is an electrochemical measuring device for transcutaneous measurement and of the type having a semi-permeable membrane 8 mounted by means of an elastic ring 9. The measuring device is intended for determining the partial pressure of the gas, preferably oxygen or carbon dioxide, passing through the skin tissue of a patient. When the measuring device is to be used it should therefore be mounted on a selected area of the skin surface of a patient. The measuring device may for example be fastened to the skin by means of an adhesive ring 17 of the type shown in FIG. 1 and provided with adhesives at both sides. Such adhesive rings 17 may be arranged on a sheet or foil 18 serving as a protecting sheet for the adhesive layer on one side of the rings. When the measuring device is to be mounted on a patient on adhesive ring 17 is removed from the sheet so that the adhesive layer on one side of the ring becomes exposed, vide FIG. 2. The adhesive ring is now mounted on the mounting member 12 with the exposed adhesive layer facing the skin abutment surface of the flange 13, and a protective layer 19 at the other side of the ring 17 is then removed as illustrated in FIG. 3. The mounting member or ring 12 may now be adhered to the selected area of the skin 20 of the patient and the electrode sensor 10 may thereafter be mounted on the mounting member 12 by means of the thread connection 15, 16 as illustrated in FIGS. 4-6.

Figure 6:
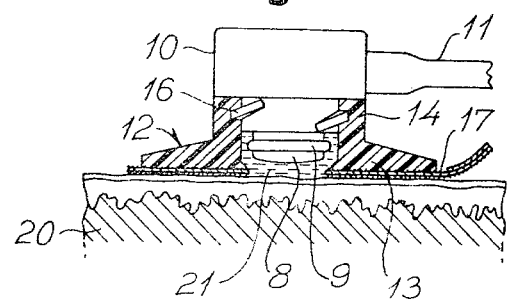
FIG. 6 is the same as FIG. 5, but the sensor is shown in its fully mounted position.

In the mounted condition of the electrode sensor 10 its inner end provided with the semi-permeable membrane 8 extends into the annular mounting member 12 to such an extent that the membrane 8 is positioned spaced from the surface of the skin 20, vide FIG. 6. This spacing may, for example be of the order 0.1–0.5 mm. The membrane 8, the opposite skin surface 20, and the surrounding inner wall of the mounting ring 12 define a closed measuring chamber which is preferably filled with a gel 21 or another suitable liquid or medium. Gases, such as oxygen and carbon dioxide, will now diffuse from the blood vessels of the patient through the skin tissue and into the said measuring chamber so that the partial gas pressures within that chamber will soon become representative of the arterial partial gas pressures. The electrode sensor 10 communicating with the measuring chamber through the semi-permeable membrane may then continuously measure the partial pressure of the interesting gas, whereby the condition of the patient may be surveyed. When after a certain time of use the electrode sensor 10 has to be calibrated, or the membrane has to be replaced, or the sensor has to be removed from the patient for some other reason this may easily and quickly be accomplished by rotating the sensor a fraction of a turn in relation to the mounting member 12 fastened to the skin 20 whereby the thread connection 15, 16 is released. The mounting ring 12 may remain fastened to the skin of the patient till another sensor is mounted, or the calibrated sensor may be remounted on the mounting ring, and thereby it is ensured that the measuring zone of the skin will be exactly the same as before. Furthermore, it is preferred that the medium used within the measuring chamber is of the same or of a similar type as the medium in which the electrode is calibrated in vitro. By these measures it is possible to substantially reduce the risk of errors in measurement.

Figure 7:
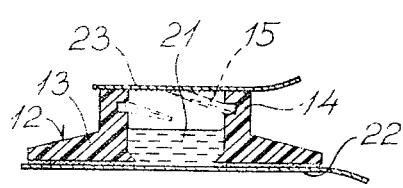
FIG. 7 is a sectional view of a modified embodiment of the mounting member intended to be used only once.

When the measurements have been terminated the mounting member 12 is removed from the patient's skin and may thereafter be cleaned and made ready for another use. However, as the mounting ring may be made rather cheaply, for example of plastic material, it is suited to be used only once whereby the time consuming cleaning is avoided. When the mounting ring is of the disposable type its skin abutment surface may be formed by an adhesive layer covered by a protecting sheet when sold to the user, and the rather complicated use of separate adhesive rings is avoided. FIG. 7 shows a modified embodiment of the mounting member 12 further facilitating the mounting procedure. As proposed above the skin abutment surface of this mounting ring is formed by an adhesive layer covered by a protecting sheet 22 and the opposite end of the mounting ring is covered and closed by a covering sheet 23. The inner space of the mounting member defined between the sheets 22 and 23 may totally or partly be filled with a gel 21 or another liquid or pasty medium. When the mounting member shown in FIG. 7 is to be used, the user only has to remove the sheets 22 and 23 and the application of a separate adhesive ring as well as introduction of gel into the mounting ring 12 are avoided.

FIGS. 8-10 show a further embodiment of the measuring device according to the invention and in these Figures the parts corresponding to parts of the embodiments shown in FIGS. 3-7 have the same reference numerals, but increased by 100. Thus, the measuring device shown in FIGS. 8-10 comprises an electrode sensor 110 connected to an electric cable 111, and a ring shaped mounting member 112 having a radial flange 113 and an axial collar or neck 114. In the skin contacting surface of the mounting member an annular recess or groove 124 is formed. Through bores 125 the groove 124 communicates with connecting suction tubes 126 extending axially from the mounting member and adapted to be connected to suction conduits or flexible tubes, not shown, communicating with a vacuum source of some kind. In this manner the mounting member 112 may be adhered to the skin of the patient by suction when the skin contacting surface of the mounting ring is placed in contact with the skin.

The electrode sensor 110 and the mounting ring 112 may be locked together by means of a special snap fastening mechanism. This locking mechanism comprises a locking element 127 mounted within the electrode sensor 110 and having a number of obliquely upwardly extending resilient detent members 128 each having a locking nose 129 at their free end. The detent members 128 extend outwardly through a number of axial slots formed in a sleeve-like releasing member 131 surrounding the locking element 127 and being axially displaceable in relation to this locking element and to the electrode sensor 110. When the electrode sensor 110 is inserted into the mounting ring 112 with the release member 131 in its lower position the locking noses 129 may resiliently engage with an annular recess or channel 132 formed at the inner side of the mounting member, whereby the sensor and the mounting member are locked together. When it is desired to remove the sensor 110 from the mounting member 112 the release member 131 is displaced upwardly from the position shown in FIG. 9 to that illustrated in FIG. 10. The lower part of the sleeve-like release member will then engage with the resilient detent members 128 and move them radially inwardly so that the locking noses 129 are moved out of engagement with the locking recess 132 in the mounting member 112.

It should be understood that various modifications of the embodiment described above may be made without departing from the scope of this invention. As an example, the sensor and the mounting member may be locked together by any suitable releasable locking members other than those shown on the drawings.

We claim:

1. An electrochemical measuring device for transcutaneous measurement of the partial pressure of a gas, said electrochemical measuring device comprising:
   a sensor unit including an electrochemical type sensor responsive to a gas to be measured, and a semipermeable membrane permeable by the gas to be measured and covering the electrochemical type sensor for permitting the gas to be measured to reach the electrochemical type sensor;
   an annular mounting member having a front annular skin opposing surface for being adhered in use to the skin of a patient and an opposite back for being spaced in use from the skin of the patient, a stop surface backward of said front annular skin opposing surface, and an open bore extending through the annular mounting member and opening at the front annular skin opposing surface and at the back of the annular member; and
   connecting means for releasably connecting said sensor unit to the back of said annular mounting member in a position to close the back opening of the bore and engage said stop surface and oriented with said semi-permeable membrane within said open bore and said connecting means being effective to permit releasing of said sensor unit from said annular mounting member and to permit connection of said sensor unit to said annular mounting member while said annular mounting member is adhered in use to the skin of a patient, said stop surface being positioned relative to said skin opposing surface such that when said sensor unit is engaged therewith said semi-permeable membrane is spaced a distance of 0.05 to 0.5 mm back from said skin opposing surface of said annular mounting member, wherein said sensor unit closing the back opening of said bore, the walls of said bore and the skin of a patient together define a measuring chamber for containing gases which permeated the skin of the patient and entered the measuring chamber including the gas which is to be measured when the measuring device is adhered in use to the skin of a patient.

2. A measuring device according to claim 1 wherein said skin opposing surface of said mounting member is a skin contacting surface in which one or more depressions or recesses are formed, and the measuring device further comprising means for connecting the depressions or recesses to a vacuum source for developing a partial vacuum effective to hold the measuring device in use to the skin of a patient.

3. A measuring device according to claim 1, wherein said releasable connecting means comprise thread means for defining threads formed on interengaging parts of the sensor unit and the mounting member, respectively, and which are effective to permit releasable connection of said sensor unit to said annular mounting member by rotating said sensor unit less than one full turn relative to said annular mounting member.

4. A measuring device according to claim 1 wherein said releasable connecting means comprise snap fastening means defining a snap fastetner formed on interengaging parts of the sensor unit and the mounting member, respectively.

5. A measuring device according to claim 4, wherein the mounting member includes an inner recess in the wall of the open bore, and wherein said snap fastening means comprises resilient detent means arranged on the sensor unit for defining a detent engageable with the inner recess formed in the mounting member, a releasing member mounted on the sensor unit and displaceable in relation thereto between a position in which the detent means are free to engage with the recess, and a releasing position in which the releasing member retains the detent means in a retracted, non-engaging position.

6. A measuring device according to claim 1, wherein the distance of said semi-permeable membrane from said skin opposing surface of 0.1 and 0.5 mm.

7. A measuring device according to claim 1, wherein said opposing surface has an adhesive layer thereon.

8. A measuring device according to claim 1, wherein said electrochemical type sensor is responsive to oxygen, and wherein said semi-permeable membrane is permeable by oxgen.

* * * * *